United States Patent [19]
Tokuhashi et al.

[11] Patent Number: 5,885,300
[45] Date of Patent: Mar. 23, 1999

[54] GUIDE APPARATUS OF INTERVERTEBRAL IMPLANT

[75] Inventors: Yasuaki Tokuhashi; Satoshi Ojima, both of Tokyo, Japan

[73] Assignee: Asahi Kogaku Kogyo Kabushiki Kaisha, Tokyo, Japan

[21] Appl. No.: 829,229

[22] Filed: Mar. 31, 1997

[30] Foreign Application Priority Data

Apr. 1, 1996 [JP] Japan .................................... 8-079113

[51] Int. Cl.[6] .................................................. A61B 17/56
[52] U.S. Cl. .............................................. 606/99; 606/104
[58] Field of Search ............................... 606/96, 104, 97, 606/98, 86, 73, 61, 60, 99

[56] References Cited

U.S. PATENT DOCUMENTS

| | | | |
|---|---|---|---|
| 5,163,940 | 11/1992 | Bourque | 606/96 |
| 5,312,412 | 5/1994 | Whipple | 606/96 |
| 5,409,493 | 4/1995 | Greenberg | 606/96 |
| 5,624,447 | 4/1997 | Myers | 606/96 |
| 5,649,930 | 7/1997 | Kertzner | 606/96 |

*Primary Examiner*—Guy V. Tucker
*Attorney, Agent, or Firm*—Greenblum & Bernstein, P.L.C.

[57] ABSTRACT

A guide apparatus of an intervertebral implant which is adapted to firmly fix an implant between adjacent corpus vertebrae includes a grip portion. A hollow inner tube is connected to the grip portion, in which an implant insertion tool can be removably inserted. A first guide projection is provided at the front end of the inner tube to protrude forward therefrom. A movable outer tube is rotatably fitted onto the inner tube. A second guide projection is provided at the front end of the movable outer tube to protrude forward therefrom.

10 Claims, 6 Drawing Sheets

GUIDE APPARATUS OF INTERVERTEBRAL IMPLANT

BACKGROUND OF THE INVENTION

1. Field of the Invention

The present invention relates to a guide apparatus (guide tool) which is adapted to insert and screw-engage an implant between adjacent corpus vertebrae to cure a degenerative disease of a corpus vertebra such as a cervical vertebra.

2. Description of the Related Art

In order to cure the degenerative disease called cervical vertebra, in a known operation, a screw (implant) is screw-engaged in a subluxation portion between an atlas (first cervical vertebra) and a second cervical vertebra. However, in this operation, there is a possibility that the spinal cord or nerve root which exists very close to the screw-engaging portion may be injured during the operation. To avoid this, the operation requires a long time, thus resulting in a heavy burden on a doctor as well as a patient.

SUMMARY OF THE INVENTION

It is an object of the present invention to provide a guide apparatus of an implant in which neither the spinal cord nor the nerve root are injured during the operation to firmly fix an implant, such as a screw between adjacent cervical vertebrae, thus leading to a safe operation.

To achieve the object mentioned above, according to an aspect of the present invention, there is provided a guide apparatus of an intervertebral implant which is adapted to firmly fix an implant between adjacent corpus vertebrae, comprising a grip portion; a hollow inner tube connected to the grip portion, in which an implant insertion tool can be removably inserted; a first guide projection provided at the front end of the inner tube to protrude forward therefrom; a movable outer tube which is at least rotatably fitted onto the inner tube; and, a second guide projection provided at the front end of the movable outer tube to protrude forward therefrom.

With this arrangement, upon attachment of the inner tube and the outer tube to the implant insertion portion, the guide apparatus is inserted while pressing the first guide projection and the second guide projection against the side portion of the spinal cord and the side portion of the nerve root, respectively. Then the movable outer tube is rotated. Thus, the nerve root is not injured by the second guide projection during the movement of the movable outer tube. The operation to insert and firmly fix the implant is carried out by successively inserting tools, such as a drill and a screw driver, etc., in the inner tube after the setting of the guide apparatus is completed.

Preferably, the movable outer tube is movable also in the axial direction thereof relative to the inner tube. The movable outer tube can be provided with an operation knob integral therewith, which extends in the radial direction.

The first and second guide projections are parallel to each other.

The first guide projection is connected to the outer peripheral surface of the inner tube to prevent the movable outer rube from being disengaged from the inner tube and to restrict the relative rotation of the movable outer tube within one turn.

The guide apparatus further comprises an operation knob provided on the movable outer tube to rotate and axially move the tube.

The relative rotational position and relative axial position between the first and second projections is adjustable.

The present disclosure relates to subject matter contained in Japanese Patent Application No. 08-79113 (filed on Apr. 1, 1996) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENT

Figure 1:
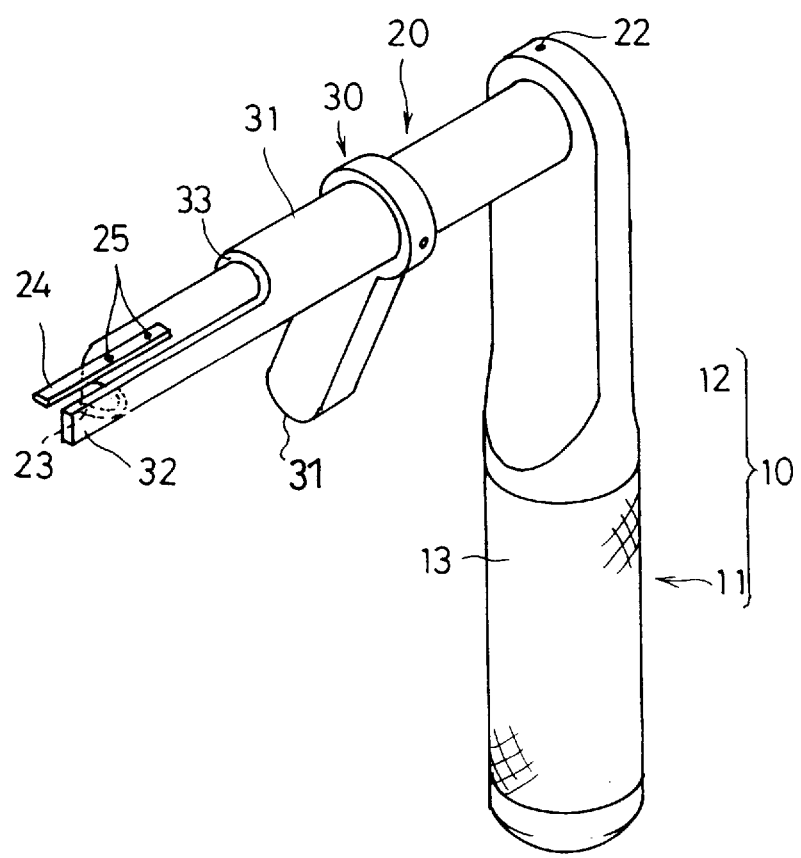
FIG. 1 is a perspective view of a guide apparatus of an intervertebral implant according to an embodiment of the present invention.
Figure 2:
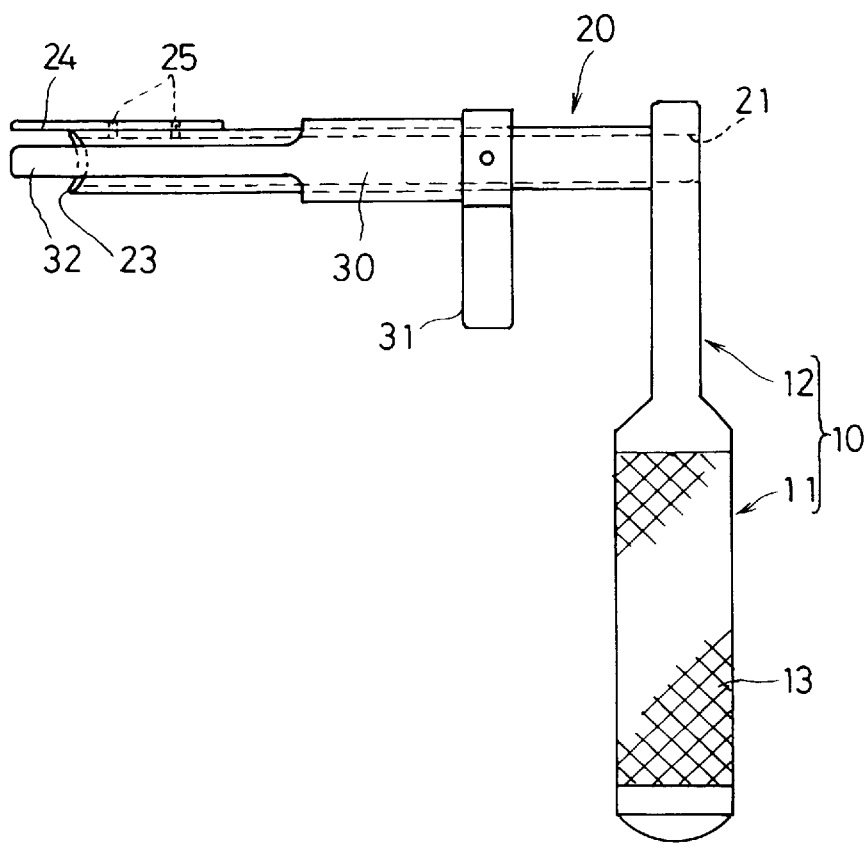
FIG. 2 is a front elevational view of the guide apparatus shown in FIG. 1.
Figure 3:
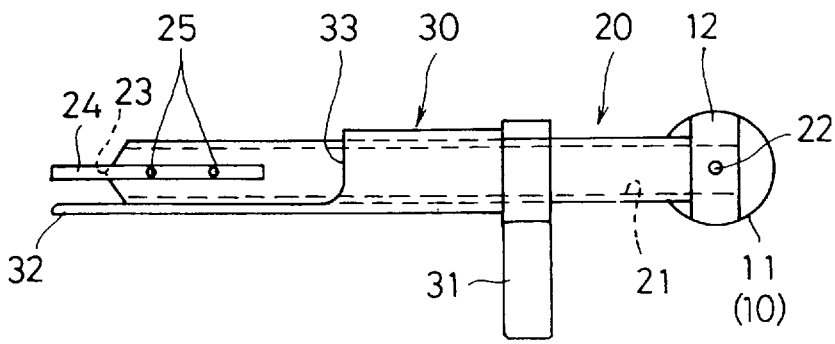
FIG. 3 is a plan view of the guide apparatus shown in FIG. 1.
Figure 4:
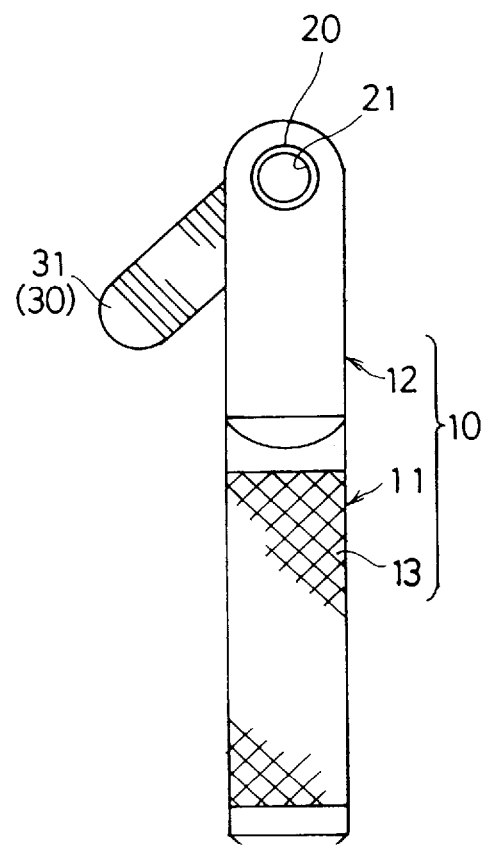
FIG. 4 is a side elevational view of the guide apparatus shown in FIG. 1.

FIGS. 1 through 4 show an embodiment of a guide apparatus of an intervertebral implant according to the present invention. The apparatus is comprised of a handle portion (grip portion) 10, a hollow inner cylinder (tube) 20 and a movable outer cylinder (tube) 30. The handle portion 10 is in a form of a column and is provided with a cylindrical portion 11 and a flat portion 12, the front end of which is connected to one end of the inner tube 20. The cylindrical portion 11 is provided with an antiskid knurl 13 to enable a firm grip.

The inner tube 20 is provided with an opening 21 at one end thereof, which opens into the flat portion 12 of the handle portion 10. The inner tube 20 is secured to the flat portion 12 by means of a screw 22 at a right angle. The inner tube 20 is provided on the other end with a sharp tip 23 defined by two flat front surfaces. A first guide projection 24 is secured to the upper surface portion of the inner tube 20 that defines the sharp tip 23 in FIG. 2 by means of screws 25 after the inner tube 20 is fitted in the movable outer tube 30. The first guide projection 24 extends forward from the inner tube 20 in parallel with the axis of the inner tube 20.

The movable outer tube 30 is fitted onto the outer peripheral surface of the inner tube 20 to rotate and move in the axial direction. The outer tube 30 is provided, on the end thereof adjacent to the handle portion 10, with a radially extending operation knob 31. The outer tube 30 is provided on the other end with a second guide projection 32. The second guide projection 32 extends forward in parallel with the axis of the movable outer tube 30 and the first guide projection 24. The movable outer tube 30 has an end surface 33 which abuts against the end surface of the first guide projection 24 of the inner tube 20 to prevent the outer tube from being disengaged from the inner tube 20. When the second guide projection 32 abuts against one of the side surfaces of the first guide projection 24, the relative rotation of the outer tube 30 is restricted. Namely, the outer tube 30 can rotate relative to the inner tube 20 by less than one turn.

Figure 5:
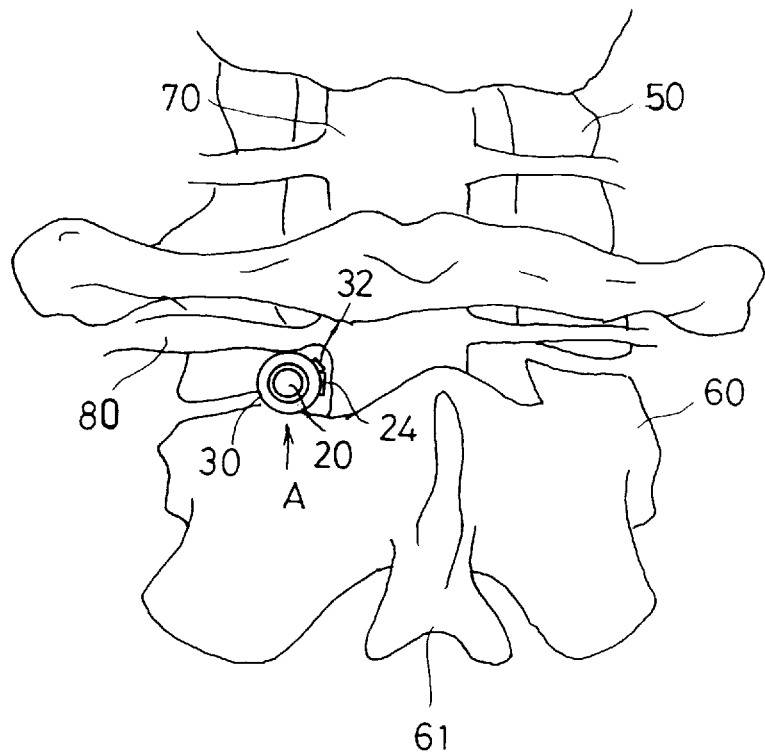
FIG. 5 is a schematic back view of a portion of a cervical vertebra to be subjected to an operation using the guide apparatus of an intervertebral implant according to the present invention.
Figure 6:
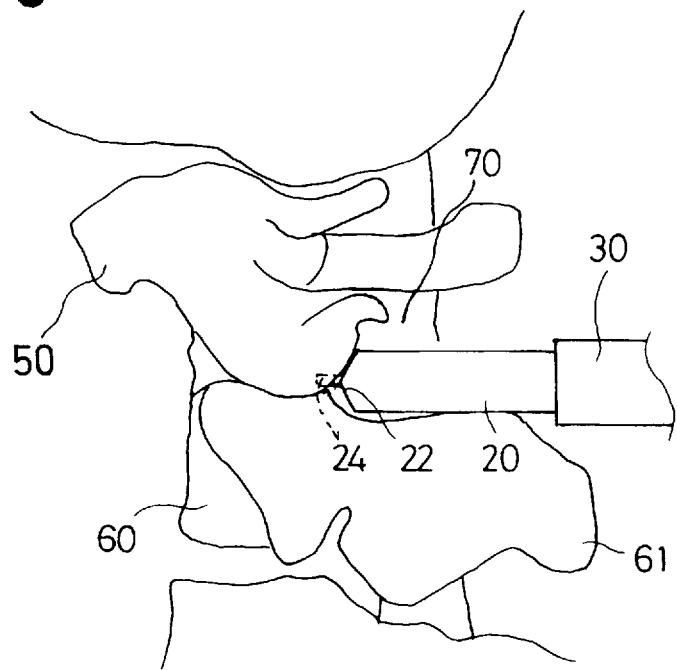
FIG. 6 is a side elevational view of FIG. 5.
Figure 7:
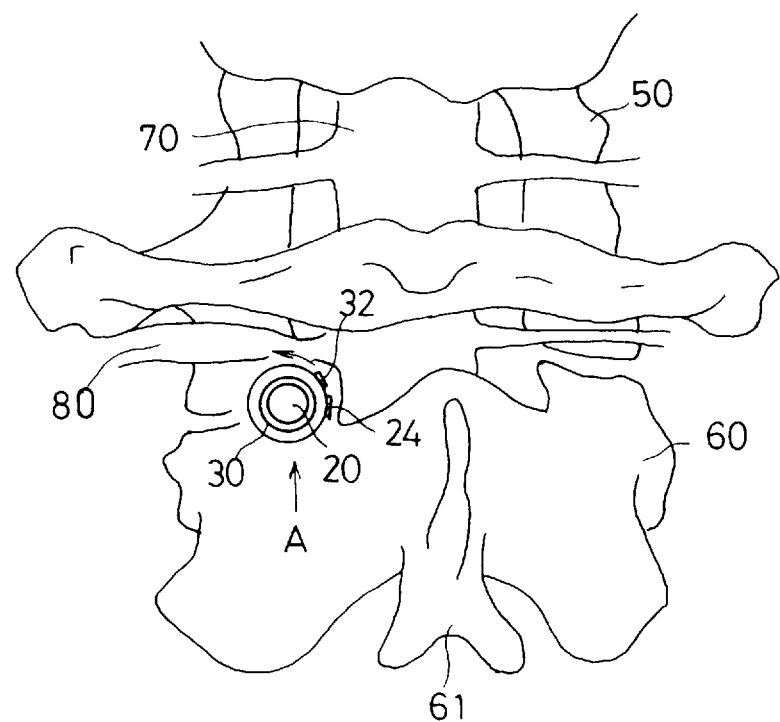
FIG. 7 is a back view of an operation portion of a cervical vertebra, shown in a position different from FIG. 5.
Figure 8:
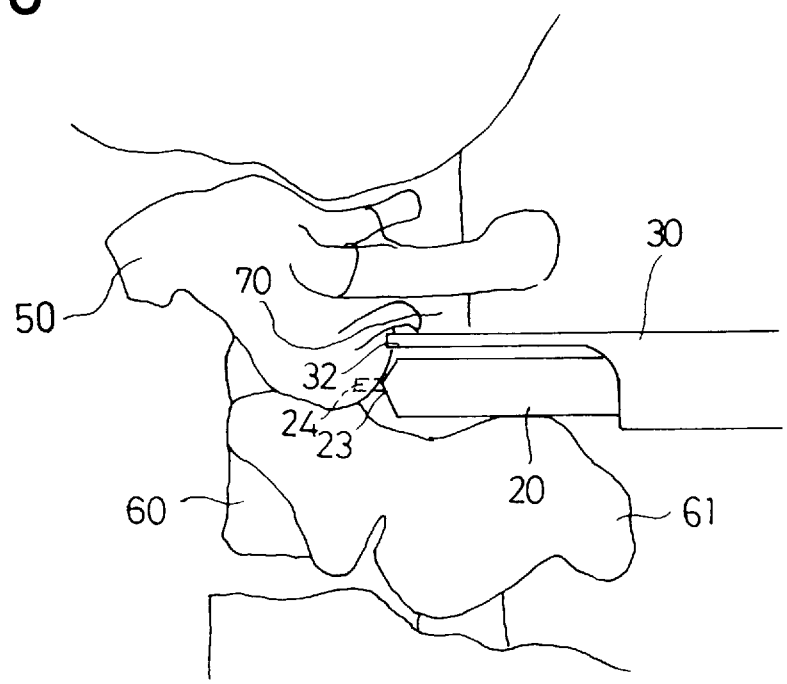
FIG. 8 is a side view of FIG. 5.

FIGS. 5 through 10 show an operation method using a guide apparatus of an intervertebral implant constructed as above, in which a screw 90 (as an implant) is firmly screw-engaged in the portion "A" between an atlas (first cervical vertebra) 50 and a second cervical vertebra 60. First, the operator holds the handle portion 10 and presses the inner tube 20 onto the portion "A" without interfering with the spinal cord 70 or nerve roots 80, as can be seen in FIGS. 5 and 6. Note that no slip of the inner tube 20 occurs due to the sharp tip 23 thereof. The first guide projection 24 is pressed against the side portion of the spinal cord 70 without injuring the same. Thereafter or simultaneously with the foregoing operation, the outer tube 30 is forced inward with the second guide projection 32 being located so as not to interfere with the spinal cord 70 or nerve root 80. Then the movable tube 30 is rotated so that the nerve root 80 is raised by the second guide projection 32, as can be seen in FIGS. 7 and 8. It should be noted here that since the movable outer tube 30 is movable in the axial direction, the second guide projection 32 can smoothly rotate along the cervical vertebra having depressions and projections without interfering with the same. In this state, the spinal cord 70 and the nerve root 80 are located outside (i.e., fully retracted from) the center axial hole of the inner tube 20. In the drawings, 61 designates the spine of the second cervical vertebra 60.

Figure 9:
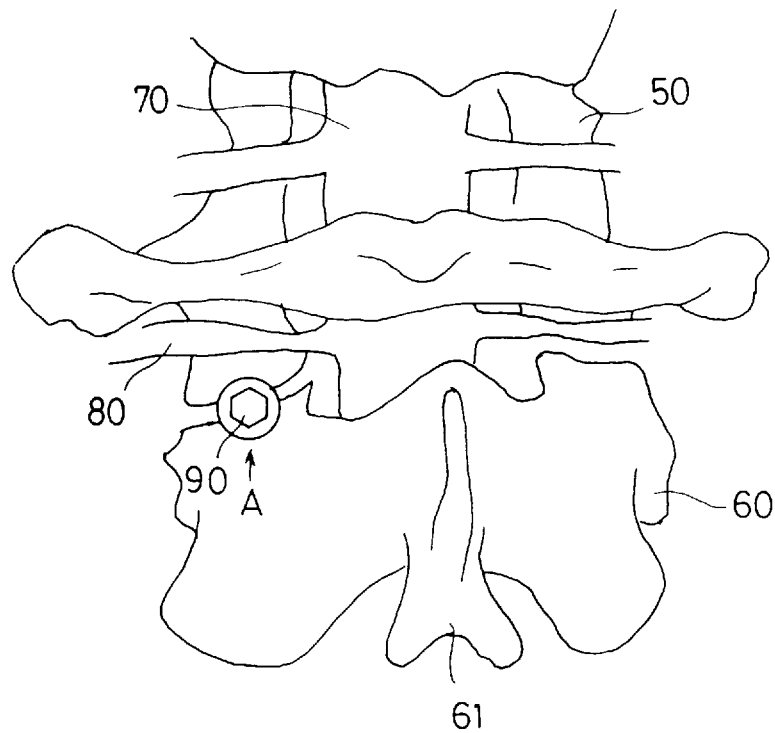
FIG. 9 is a back view of an operation portion of a cervical vertebra, shown in a position different from FIG. 5 or FIG. 7; and, FIG. 10 is a side view of FIG. 9.
Figure 10:
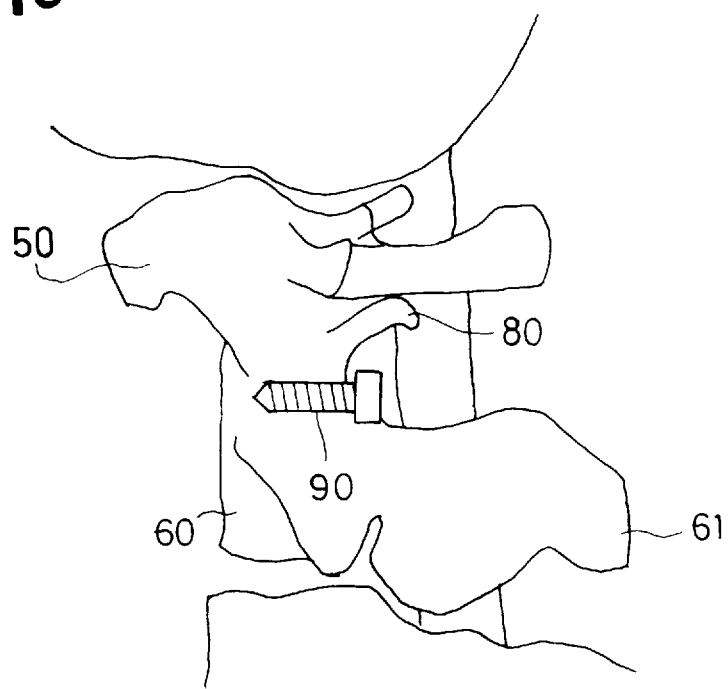

In this position, a drill (not shown) is inserted through the end opening 21 of the inner tube 20 to pierce a preliminary hole in the adjoining portion of the atlas (first cervical vertebra) 50 and the second cervical vertebra 60. Then the drill is removed and a tap (not shown) is inserted to form a thread in the preliminary hole. Thereafter, the screw 90 is inserted in the inner tube 20 through the end opening 21 thereof and is rotated and fastened in the threaded preliminary hole with the help of a screwdriver inserted in the inner tube 20 (FIGS. 9 and 10). The tapping operation or drilling operation can be dispensed with, depending on the mode of the surgical operation.

In the operation mentioned above, the first guide projection 24 of the inner tube 20 prevents the spinal cord 70 from being injured by the drill, tap, or screw 90. Similarly, the second guide projection 32 of the outer tube 30 prevents the nerve root 80 from being injured by the drill, tap, or screw. Consequently, if the first setting operation of the inner tube 20 and the movable outer tube 30 is carefully carried out, the formation of the preliminary hole and the screw-engagement of the screw 90 subsequent to the first setting operation can be easily and safely effected.

Although the screw is used as an implant in the illustrated embodiment, the guide apparatus according to the present invention can be equally applied to an implant other than the screw.

As can be understood from the above discussion, according to the present embodiment, a safe guide apparatus of an implant operation to firmly fix the implant between the adjacent cervical vertebrae in which no injury of the spinal cord or nerve root, etc., takes place can be provided.

What is claimed is:

1. A guide apparatus of an intervertebral implant which is adapted to fix an implant between adjacent corpus vertebrae, comprising:
   a grip portion;
   a hollow inner tube connected to the grip portion, in which an implant insertion tool can be removably inserted;
   a first guide projection provided at the front end of the inner tube to protrude forward therefrom;
   a movable outer tube which is rotatably fitted onto the inner tube; and,
   a second guide projection provided at the front end of the movable outer tube to protrude forward therefrom;
   wherein said first guide projection and said second guide projection are parallel to each other.

2. A guide apparatus of an intervertebral implant according to claim 1, wherein said movable outer tube is movable in the axial direction thereof relative to the inner tube.

3. A guide apparatus of an intervertebral implant according to claim 1, wherein said movable outer tube is provided with an operation knob integral therewith, which extends in the radial direction.

4. A guide apparatus of an intervertebral implant according to claim 1, wherein said first guide projection is connected to the outer peripheral surface of the inner tube to prevent the outer tube from disengaging said inner tube and restricting a relative range of rotation of the outer tube.

5. A guide apparatus of an intervertebral implant according to claim 4, wherein said first guide projection restricts the relative rotation of said outer tube within one turn.

6. The guide apparatus of claim 1, wherein said second guide projection is integral with said movable outer tube.

7. The guide apparatus of claim 1, wherein said movable outer tube has a central axis, and said second guide projection extends parallel with said axis.

8. A guide apparatus of an intervertebral implant which is adapted to fix an implant between adjacent corpus vertebrae, comprising:
   a handle portion in a form of a rod;
   a hollow inner tube connected at one end of said handle portion at a right angle, in which said implant insertion tool can be removably inserted;
   a first guide projection provided at the front end of the inner tube to protrude forwardly therefrom;
   a movable outer tube which is movably fitted onto the inner tube;
   an operation knob provided on said movable outer tube to rotate and axially move the outer tube; and,
   a second guide projection provided at the front end of the movable outer tube to protrude forwardly therefrom;
   wherein relative rotational position and relative axial position between said first and second projections is adjustable; and
   wherein said first and second guide projections are parallel to each other.

9. The guide apparatus of claim 8, wherein said second guide projection is integral with said movable outer tube.

10. The guide apparatus of claim 8, wherein said movable outer tube has a central axis, and said second guide projection extends parallel with said axis.

* * * * *